US010352901B2

(12) United States Patent
Suzuki et al.

(10) Patent No.: US 10,352,901 B2
(45) Date of Patent: Jul. 16, 2019

(54) PARTICULATE MEASUREMENT SYSTEM

(71) Applicant: NGK Spark Plug Co., LTD., Nagoya (JP)

(72) Inventors: Isao Suzuki, Ichinomiya (JP); Kazunari Kokubo, Komaki (JP)

(73) Assignee: NGK SPARK PLUG CO., LTD., Nagoya (JP)

(*) Notice: Subject to any disclaimer, the term of this patent is extended or adjusted under 35 U.S.C. 154(b) by 162 days.

(21) Appl. No.: 15/371,961

(22) Filed: Dec. 7, 2016

(65) Prior Publication Data

US 2017/0160234 A1 Jun. 8, 2017

(30) Foreign Application Priority Data

Dec. 8, 2015 (JP) .................................. 2015-239488

(51) Int. Cl.
*G01N 27/68* (2006.01)
*G01M 15/10* (2006.01)
(Continued)

(52) U.S. Cl.
CPC .......... *G01N 27/68* (2013.01); *G01M 15/102* (2013.01); *G01N 15/0656* (2013.01); *G01N 2015/0046* (2013.01)

(58) Field of Classification Search
CPC ............... G01N 27/68; G01N 15/0656; G01N 2015/0046; G01N 1/2252; G01N 27/70;
(Continued)

(56) References Cited

U.S. PATENT DOCUMENTS 9,053,912 B2* 6/2015 Kokubo ............... H01J 49/022
2007/0115339 A1 5/2007 Matsuzaki et al.
(Continued)

FOREIGN PATENT DOCUMENTS

JP 2007-144667 A 6/2007
JP 2013-195069 A 9/2013
(Continued)

OTHER PUBLICATIONS

English Machine Translation of Kokubo JP 2015-36647.*
Office Action dated Apr. 24, 2018 for the corresponding Japanese Patent Application No. 2015-239488.

*Primary Examiner* — Lee E Rodak
(74) *Attorney, Agent, or Firm* — Leason Ellis LLP

(57) ABSTRACT

Particulate measurement processing executed by a sensor control section of a particulate measurement system includes a step of stopping voltage conversion by a first isolation transformer and a second isolation transformer, a step of obtaining correction information B, and a step of correcting ion current A through use of the correction information B. The correction information B reflects improper current generated through particulates, etc. (soot or the like) adhering to a particulate sensor. The ion current A (signal current $I_{esc}$) is corrected through use of the correction information B, and the amount of soot S is computed through use of the corrected ion current A'. As a result, it is possible to measure the amount of the soot S (the amount of particulates) while suppressing the influence of the improper current.

6 Claims, 7 Drawing Sheets

(51) Int. Cl.
*G01N 15/06* (2006.01)
*G01N 15/00* (2006.01)

(58) Field of Classification Search
CPC ........... G01N 15/0606; G01N 33/0027; G01N 33/0036; G01N 2001/2285; G01N 2001/244; G01N 2291/02408; G01N 27/4077; G01N 27/62; G01N 33/0011; G01N 33/0073; G01M 15/102; F01N 2560/05; F01N 13/008; F01N 11/00; F01N 11/007; F01N 2900/1411; F02D 41/222; F02D 2041/2003
See application file for complete search history.

(56) References Cited

U.S. PATENT DOCUMENTS

| | | | |
|---|---|---|---|
| 2014/0352405 A1 | 12/2014 | Motomura et al. | |
| 2015/0114087 A1* | 4/2015 | Sugiyama | G01M 15/102 73/28.01 |
| 2015/0120229 A1* | 4/2015 | Sugiyama | G01N 15/0606 702/85 |

FOREIGN PATENT DOCUMENTS

| | | |
|---|---|---|
| JP | 2015-36647 A | 2/2015 |
| JP | 2015-215207 A | 12/2015 |

* cited by examiner

PARTICULATE MEASUREMENT SYSTEM

This application claims the benefit of Japanese Patent Application No. 2015-239488, filed Dec. 8, 2015, which is incorporated herein in its entirety by reference.

FIELD OF THE INVENTION

The present invention relates to a particulate measurement system which measures the amount of particulates such as soot contained in a gas under measurement.

BACKGROUND OF THE INVENTION

Conventionally, there has been known a particulate measurement system which measures the amount of particulates (e.g., soot) contained in a gas under measurement (for example, exhaust gas discharged from an internal combustion engine or the like) (see, for example, Japanese Patent Application Laid-Open (kokai) No. 2013-195069).

Such a particulate measurement system includes a particulate sensor which is exposed to the gas under measurement and detects particulates. The particulate sensor includes an ion generation section, an electrification chamber, and a trapping section. Also, in use, the particulate sensor is connected to a sensor drive section for driving the particulate sensor.

Through use of ions generated at the ion generation section by means of corona discharge, the particulate measurement system causes the ions to adhere to at least a portion of particulates contained in the gas under measurement in the electrification chamber to produce electrified particulates. The particulate measurement system measures the amount of particulates on the basis of the amount of the electrified particulates (in other words, the amount of ions trapped by the trapping section). Specifically, a particulate computation section provided in the sensor drive section (in a sensor control section) detects a signal current which flows between a primary-side reference potential representing the reference potential of a primary coil of an isolation transformer for corona discharge and a secondary-side reference potential representing the reference potential of a secondary coil of the isolation transformer for corona discharge, the signal current flowing in accordance with the amount of the electrified particulates, and computes (measures) the amount of particulates by using this signal current.

Problem to be Solved by the Invention

However, the particulate measurement system as described above has a problem in that when particulates (soot, etc.) adhere to the particulate sensor, the accuracy in measuring the amount of particulates lowers or measurement of the amount of particulates becomes impossible. Also, the accuracy in measuring the amount of particulates may lower due to, for example, time-course deterioration of circuit components which constitute the sensor drive section connected to the particulate sensor or deterioration of the insulation between the circuit components.

Namely, for example, when the insulation resistance of an insulating member which constitutes the particulate sensor lowers due to particulates, etc., adhering to the particulate sensor, an improper current may be superimposed on the signal current flowing between the primary-side reference potential and the secondary-side reference potential. Also, an improper current may be superimposed on the signal current due to the time-course deterioration of the circuit components or the deterioration of the insulation between the circuit components in the sensor drive section.

An object of the present invention is to provide a particulate measurement system which suppresses a decrease in the accuracy of measurement of particulates due to improper current.

SUMMARY OF THE INVENTION

Means for Solving the Problem

A particulate measurement system for measuring an amount of particulates contained in a target gas according to one aspect of the present invention comprises a particulate sensor that is configured to detect particulates and a sensor drive section that is configured to drive the particulate sensor. The particulate sensor includes an ion generation section, an electrification chamber, and a trapping section. The sensor drive section includes an isolation transformer for corona discharge, a corona discharge control section, a particulate computation section, a voltage conversion stoppage section, a correction information obtaining section, and a correction section.

The ion generation section generates ions by means of corona discharge. The electrification chamber is provided so as to cause the ions to adhere to at least a portion of the particulates contained in the target gas to thereby produce electrified particulates. The trapping section traps at least a portion of the ions generated by the ion generation section but not used for the electrification of the particulates.

The isolation transformer for corona discharge is an isolation transformer which has a primary coil and a secondary coil and performs voltage conversion for electric power used for the corona discharge, and the secondary coil of the isolation transformer for corona discharge is connected to the ion generation section.

The particulate computation section detects a signal current which flows between a primary-side reference potential representing the reference potential of the primary coil of the isolation transformer for corona discharge and a secondary-side reference potential representing the reference potential of the secondary coil of the isolation transformer for corona discharge and which flows in accordance with the amount of the electrified particulates. The corona discharge control section detects a secondary-side current flowing from the trapping section to the secondary-side reference potential and controls the amount of electric power supplied from the isolation transformer for corona discharge to the ion generation section through use of the secondary-side current such that the amount of ions generated from the ion generation section approaches a predetermined target value.

The voltage conversion stoppage section stops the voltage conversion by the isolation transformer for corona discharge. When the voltage conversion is stopped by the voltage conversion stoppage section, the correction information obtaining section obtains, as information for correction, the signal current detected by the particulate computation section or the amount of the particulates computed by the particulate computation section. When the voltage conversion by the isolation transformer for corona discharge is performed, the correction section corrects, through use of the information for correction, the signal current detected by the particulate computation section or the amount of the particulates computed by the particulate computation section.

In the case where the voltage conversion by the isolation transformer for corona discharge is stopped by the voltage conversion stoppage section, the generation of ions in the ion generation section is stopped. In such a state, since no electrified particulate is produced in the electrification chamber, the signal current does not change in accordance with the amount of electrified particulates.

However, when an improper current is generated through, for example, particulates having adhered to the particulate sensor or an improper current is generated due to the influence of the sensor drive section side, the improper current is superimposed on the signal current and is detected as the signal current. Therefore, the signal current detected by the particulate computation section or the computation result (the amount of particulates) computed by the particulate computation section when the voltage conversion is stopped by the voltage conversion stoppage section changes in accordance with the improper current. Namely, the information for correction obtained by the correction information obtaining section reflects the improper current.

Because of this, it is possible to measure particulates, while suppressing the influence of the improper current, by correcting, through use of the information for correction, the signal current detected by the particulate computation section or the amount of particulates computed by the particulate computation section.

Accordingly, since this particulate measurement system includes the voltage conversion stoppage section, the correction information obtaining section, and the correction section, and corrects, through use of the information for correction, the signal current or the amount of particulates detected by the particulate computation section, it can measure particulates while suppressing the influence of the improper current. Therefore, this particulate measurement system can suppress a decrease in the accuracy of measurement of particulates due to improper current.

In the above-described particulate measurement system, the voltage conversion stoppage section may be configured to stop the voltage conversion when it receives a stoppage permission signal from outside the sensor drive section.

By receiving, as the stoppage permission signal from outside the sensor drive section, for example, a signal which notifies a time at which the target gas contains no particulate (or a time at which the amount of particulates is small), it becomes possible to determine whether or not the present point in time is the time at which the target gas contains no particulate (or the time at which the amount of particulates is small). Thus, it is possible to obtain the information for correction while avoiding times at which particulates are likely to be generated (in other words, times at which the necessity of measuring particulates is high).

Accordingly, since this particulate measurement system can avoid an increase in the time over which the measurement of particulates is stopped in a period during which the necessity of measuring particulates is high, the particulate measurement system can suppress a decrease in the particulate measurement accuracy.

Next, in the above-described particulate measurement system, the voltage conversion stoppage section may be configured to stop the voltage conversion at predetermined stoppage intervals.

By stopping the voltage conversion periodically as described above, it is possible to periodically obtain the information for correction and correct the amount of particulates on the basis of the information for correction updated at the stoppage intervals. As a result, even in an application in which particulates are measured over a long period, since the information for correction is updated at the stoppage intervals, the amount of particulates can be corrected properly irrespective of a change in the state of the particulate sensor (in other words, a change in the state of adhesion of particulates, etc.).

Therefore, according to this particulate measurement system, even when the state of adhesion of particulates, etc. in the particulate sensor changes, the amount of particulates can be corrected properly, whereby a decrease in the particulate measurement accuracy can be suppressed.

Next, in the above-described particulate measurement system, the particulate sensor may be attached to an exhaust pipe of an internal combustion engine, and the voltage conversion stoppage section may be configured to stop the voltage conversion when a cumulative operation time of the internal combustion engine exceeds a predetermined stoppage time.

In the case of a particulate sensor attached to the exhaust pipe of the internal combustion engine, particulates such as soot contained in exhaust gas may adhere to the particulate sensor, and the longer the operation time of the internal combustion engine, the greater the possibility of adhesion of the particulates.

Therefore, by stopping the voltage conversion and obtaining the information for correction at the timing at which the cumulative operation time of the internal combustion engine exceeds the stoppage time, it is possible to obtain the information for correction corresponding to the time-course deterioration of the particulate sensor and the time-course deterioration of the sensor drive section. As a result, it is possible to obtain the information for correction corresponding to the state of adhesion of particulates in the particulate sensor and properly correct the amount of particulates. Thus, it is possible to accurately detect, over a long period of time, the amount of particulates contained in exhaust gas (target gas) discharged from the internal combustion engine.

Effects of the Invention

Since the particulate measurement system of the present invention can measure particulates, while suppressing the influence of the improper current, by correcting the amount of particulates through use of the information for correction, the particulate measurement system can suppress a decrease in the accuracy of measurement of particulates due to improper current.

BRIEF DESCRIPTION OF THE DRAWINGS

These and other features and advantages of the present invention will become more readily appreciated when considered in connection with the following detailed description and appended drawings, wherein like designations denote like elements in the various views, and wherein:

FIGS. 1(a) and 1(b) are explanatory views used for describing the overall configuration of a particulate measurement system according to a first embodiment, wherein FIG. 1(a) is an explanatory view exemplifying a general configuration of a vehicle 500 on which a particulate measurement system 10 is mounted, and FIG. 1(b) is an explanatory view exemplifying a general configuration of the particulate measurement system 10 attached to the vehicle 500.

DETAILED DESCRIPTION OF THE INVENTION

[Modes for Carrying Out the Invention]

Embodiments to which the present invention is applied will next be described with reference to the drawings.

The present invention is not limited to the following embodiments, but can be embodied in various modes so long as the modes fall within the technical scope of the present invention.

[1. First Embodiment]
[1-1. Overall Configuration]

The configuration of a particulate measurement system according to the present embodiment will be described.

Figure 1A:
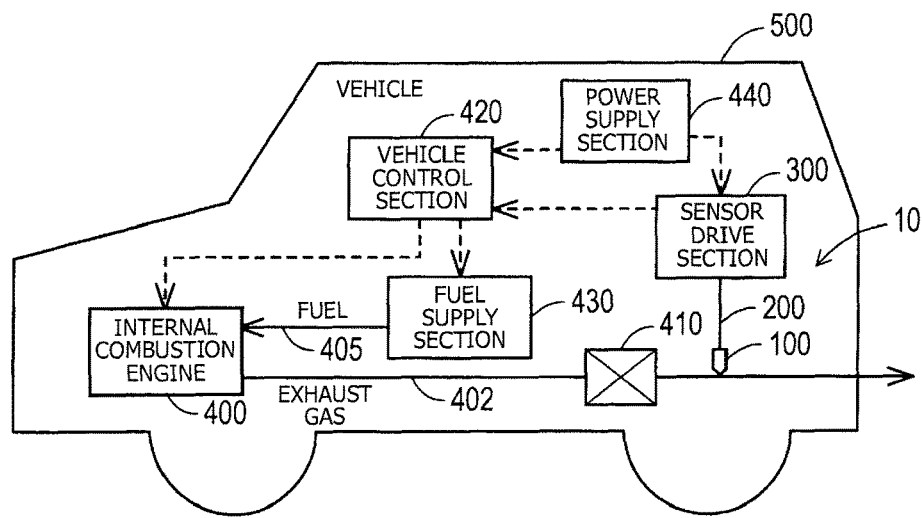
Figure 1B:
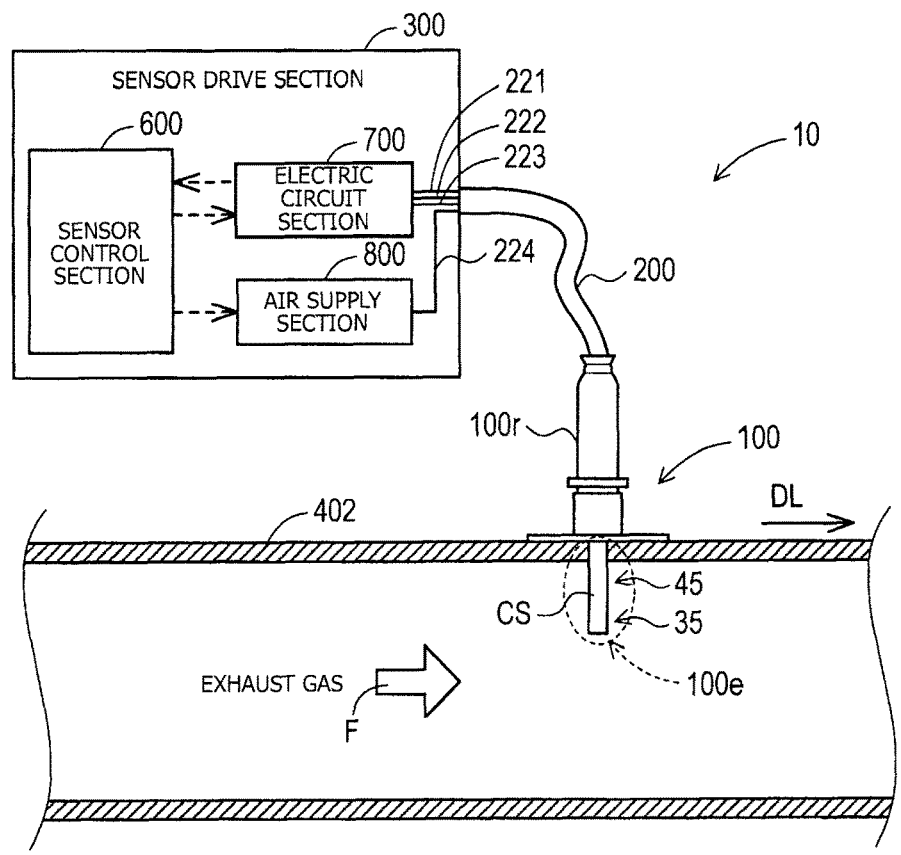

FIGS. 1(a) and 1(b) are explanatory views used for describing the overall configuration of a particulate measurement system 10 according to the first embodiment. FIG. 1(a) is an explanatory view schematically exemplifying a general configuration of a vehicle 500 on which the particulate measurement system 10 is mounted. FIG. 1(b) is an explanatory view exemplifying a general configuration of the particulate measurement system 10 attached to the vehicle 500.

The particulate measurement system 10 includes a particulate sensor 100, a cable 200, and a sensor drive section 300, and measures the amount of particulates such as soot contained in exhaust gas discharged from an internal combustion engine 400. The internal combustion engine 400, which is a power source of the vehicle 500, is a diesel engine or the like.

The particulate sensor 100 is attached to an exhaust pipe 402 extending from the internal combustion engine 400, and is electrically connected to the sensor drive section 300 through the cable 200. In the present embodiment, the particulate sensor 100 is attached to a portion of the exhaust pipe 402, which portion is located downstream of a filter apparatus 410 (for example, a DPF (diesel particulate filter)). The particulate sensor 100 outputs to the sensor drive section 300 a signal which correlates with the amount of particulates contained in the exhaust gas.

The sensor drive section 300 drives the particulate sensor 100 and detects (measures) the amount of particulates contained in the exhaust gas on the basis of the signal input from the particulate sensor 100. The "amount of particulates contained in the exhaust gas" detected by the sensor drive section 300 may be a value which is proportional to the sum of the surface areas of particulates contained in the exhaust gas or a value which is proportional to the sum of the masses of the particulates. Alternatively, the amount of particulates contained in the exhaust gas may be a value which is proportional to the number of particulates contained in a unit volume of the exhaust gas. The sensor drive section 300 is electrically connected to a vehicle control section 420 on the vehicle 500 side and outputs to the vehicle control section 420 a signal representing the detected amount of particulates contained in the exhaust gas.

In response to the signal input from the sensor drive section 300, the vehicle control section 420 controls the combustion state of the internal combustion engine 400, the amount of fuel supplied from a fuel supply section 430 to the internal combustion engine 400 through a fuel pipe 405, etc. The vehicle control section 420 may be configured to warn a driver of the vehicle 500 about a deterioration or anomaly of the filter apparatus 410, for example, when the amount of particulates contained in the exhaust gas is greater than a predetermined amount. The sensor drive section 300 and the vehicle control section 420 are electrically connected to a power supply section 440, and electric power is supplied from the power supply section 440 to the sensor drive section 300 and the vehicle control section 420.

As shown in FIG. 1(b), the particulate sensor 100 has a cylindrical distal end portion 100e, and is fixed to the outer surface of the exhaust pipe 402 such that the distal end portion 100e is inserted into the exhaust pipe 402. In the present embodiment, the distal end portion 100e of the particulate sensor 100 is inserted approximately perpendicular to an extension direction DL of the exhaust pipe 402. A casing CS of the distal end portion 100e has an inflow hole 45 and a discharge hole 35 formed on the surface of the casing CS. The inflow hole 45 is used to introduce the exhaust gas into the interior of the casing CS, and the discharge hole 35 is used to discharge the introduced exhaust gas to the outside of the casing CS. A portion of the exhaust gas flowing through the exhaust pipe 402 is introduced into the interior of the casing CS of the distal end portion 100e through the inflow hole 45. Particulates contained in the introduced exhaust gas are electrified by ions (positive ions in the present embodiment) generated by the particulate sensor 100. The exhaust gas containing the electrified particulates is discharged to the outside of the casing CS through the discharge hole 35. The internal structure of the casing CS and the specific structure of the particulate sensor 100 will be described later.

The cable 200 is attached to a rear end portion 100r of the particulate sensor 100. The cable 200 includes a first wiring line 221, a second wiring line 222, a signal line 223, and an air supply tube 224 bundled together. Each of the wiring lines 221 to 223 and the air supply tube 224, which constitute the cable 200, is formed of a flexible member. The first wiring line 221, the second wiring line 222, and the signal line 223 are electrically connected to an electric circuit section 700 of the sensor drive section 300, and the air supply tube 224 is connected to an air supply section 800 of the sensor drive section 300.

The sensor drive section 300 includes a sensor control section 600, the electric circuit section 700, and the air supply section 800. The sensor control section 600 and the electric circuit section 700 are electrically connected to each other, and the sensor control section 600 and the air supply section 800 are electrically connected to each other.

The sensor control section 600 includes a microcomputer, and controls the electric circuit section 700 and the air supply section 800. Also, the sensor control section 600 detects (measures) the amount of particulates contained in the exhaust gas from a signal supplied from the electric circuit section 700 and outputs to the vehicle control section 420 a signal representing the amount of particulates contained in the exhaust gas.

The electric circuit section 700 supplies electric power for driving the particulate sensor 100 through the first wiring line 221 and the second wiring line 222. A signal which correlates with the amount of particulates contained in the exhaust gas is input from the particulate sensor 100 to the electric circuit section 700 through the signal line 223. Using this signal input through the signal line 223, the electric circuit section 700 outputs to the sensor control section 600 a signal corresponding to the amount of particulates contained in the exhaust gas. These signals will be described in detail later.

The air supply section 800 includes a pump (not shown), and supplies high-pressure air to the particulate sensor 100 through the air supply tube 224 on the basis of an instruction from the sensor control section 600. The high-pressure air supplied from the air supply section 800 is used for drive of the particulate sensor 100. Notably, the type of the gas supplied by the air supply section 800 may be other than air.

[1-2. Particulate Sensor]

Figure 2:
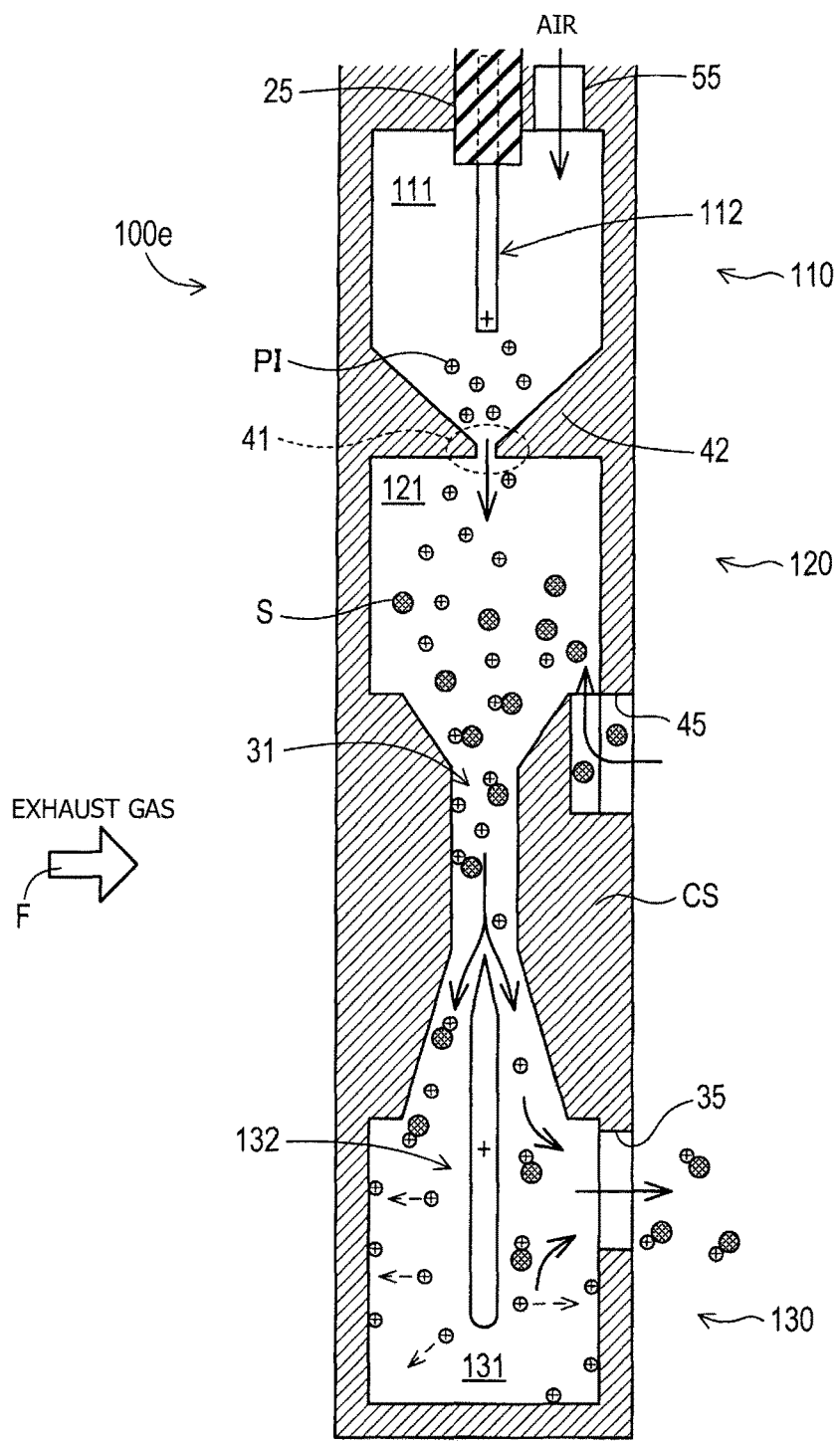
FIG. 2 is an explanatory view schematically showing a general structure of a distal end portion of a particulate sensor.

FIG. 2 is an explanatory view schematically showing a general structure of the distal end portion 100e of the particulate sensor 100.

The distal end portion 100e of the particulate sensor 100 includes an ion generation section 110, an exhaust gas electrification section 120, and an ion trapping section 130. The casing CS has a structure in which the three mechanism sections; i.e., the ion generation section 110, the exhaust gas electrification section 120, and the ion trapping section 130, are arranged in this order from the proximal end side (the upper side in FIG. 2) of the distal end portion 100e toward the distal end side (the lower side in FIG. 2) thereof (along the axial direction of the particulate sensor 100). The casing CS is formed of an electrically conductive material, and is connected to a secondary-side ground SGL (FIG. 3) through the signal line 223 (FIG. 1(b)).

The ion generation section 110 is a mechanism section for generating ions (positive ions in the present embodiment) which are supplied to the exhaust gas electrification section 120. The ion generation section 110 includes an ion generation chamber 111 and a first electrode 112. The ion generation chamber 111 is a small space formed inside the casing CS. An air supply hole 55 and a nozzle 41 are provided on the inner circumferential surface of the ion generation chamber 111. The first electrode 112 is attached such that it projects into the ion generation chamber 111. The air supply hole 55 communicates with the air supply tube 224 (FIG. 1(b)), and the high-pressure air supplied from the air supply section 800 (FIG. 1(b)) is supplied to the ion generation chamber 111 through the air supply hole 55. The nozzle 41 is a very small hole (orifice) provided near the center of a partition wall 42 which separates the ion generation section 110 and the exhaust gas electrification section 120. The nozzle 41 supplies the ions generated in the ion generation chamber 111 to an electrification chamber 121 of the exhaust gas electrification section 120. The first electrode 112 has a rod-like outer shape, and its base end portion is fixed to the casing CS via a ceramic pipe 25 in a state in which a distal end portion of the first electrode 112 is located near the partition wall 42. The first electrode 112 is connected to the electric circuit section 700 (FIG. 1(b)) through the first wiring line 221 (FIG. 1(b)).

The ion generation section 110 is configured such that, by the electric power supplied from the electric circuit section 700, a voltage (e.g., 2 to 3 kV) is applied between the first electrode 112 (positive pole) and the partition wall 42 (negative pole). As a result of application of this voltage, the ion generation section 110 produces corona discharge between a distal end portion of the first electrode 112 and the partition wall 42 to thereby generate positive ions PI. The positive ions PI generated in the ion generation section 110 are jetted into the electrification chamber 121 of the exhaust gas electrification section 120 through the nozzle 41 together with the high-pressure air supplied from the air supply section 800 (FIG. 1(b)). The jetting speed of air jetted from the nozzle 41 may be set to a speed near the speed of sound.

The exhaust gas electrification section 120 is a section for electrifying the particulates contained in the exhaust gas by positive ions PI, and includes the electrification chamber 121. The electrification chamber 121 is a small space located adjacent to the ion generation chamber 111, and communicates with the ion generation chamber 111 through the nozzle 41. Also, the electrification chamber 121 communicates with the outside of the casing CS through the inflow hole 45, and communicates with a trapping chamber 131 of the ion trapping section 130 through a gas flow passage 31. The electrification chamber 121 is configured such that, when air containing the positive ions PI are jetted from the nozzle 41, a negative pressure is created in the electrification chamber 121, and the exhaust gas located outside the casing CS flows into the electrification chamber 121 through the inflow hole 45. Therefore, the air jetted from the nozzle 41 and containing the positive ions PI and the exhaust gas flowing inward through the inflow hole 45 are mixed together within the electrification chamber 121. At that time, at least a portion of the soot S (particulates) contained in the exhaust gas flowed inward through the inflow hole 45 are electrified by the positive ions PI supplied from the nozzle 41. The air containing the electrified soot S and the positive ions PI not used for the electrification is supplied to the trapping chamber 131 of the ion trapping section 130 through the gas flow passage 31.

The ion trapping section 130 is a section for trapping ions not used for the electrification of the soot S (particulates), and includes the trapping chamber 131 and a second electrode 132. The trapping chamber 131 is a small space located adjacent to the electrification chamber 121, and communicates with the electrification chamber 121 through the gas flow passage 31. Also, the trapping chamber 131 communicates with the outside of the casing CS through the discharge hole 35. The second electrode 132 has a generally rod-like outer shape and is fixed to the casing CS such that its longitudinal direction coincides with the flow direction of air flowing through the gas flow passage 31 (the extending direction of the casing CS). The second electrode 132 is connected to the electric circuit section 700 (FIG. 1(b)) through the second wiring line 222 (FIG. 1(b)). The second electrode 132 is electrically insulated from the casing CS.

A voltage of about 100 V is applied to the second electrode 132, whereby it functions as an auxiliary electrode for assisting the trapping of positive ions not used for the electrification of the soot S. Specifically, by the electric power supplied from the electric circuit section 700, a voltage is applied to the ion trapping section 130 such that the second electrode 132 serves as a positive pole, and the casing CS constituting the electrification chamber 121 and the trapping chamber 131 serves as a negative pole. As a result, the positive ions PI not used for the electrification of soot S receive a repulsive force from the second electrode 132, whereby their advancing directions deviate to directions away from the second electrode 132. The positive ions PI whose advancing directions have been deviated are trapped by the inner circumferential walls of the trapping chamber 131 and the gas flow passage 31 which function as a negative pole. Meanwhile, the soot S to which positive ions PI have adhered also receive the repulsive force from the second electrode 132 as in the case of the positive ions PI themselves. However, since the soot S are larger in mass than the positive ions PI, the influence of the repulsive force on the advancing directions is smaller as compared with the case of the positive ions PI themselves. Therefore, the electrified soot S are discharged to the outside of the casing CS through the discharge hole 35 as a result of the flow of the exhaust gas.

The particulate sensor 100 outputs a signal showing a change in current which corresponds to the amount of positive ions PI trapped in the ion trapping section 130. The sensor control section 600 (FIG. 1(b)) detects the amount of soot S contained in the exhaust gas on the basis of the signal output from the particulate sensor 100. A method of calculating the amount of soot S contained in the exhaust gas from the signal output from the particulate sensor 100 will be described later.

[1-3. Electric Circuit Section]

Figure 3:
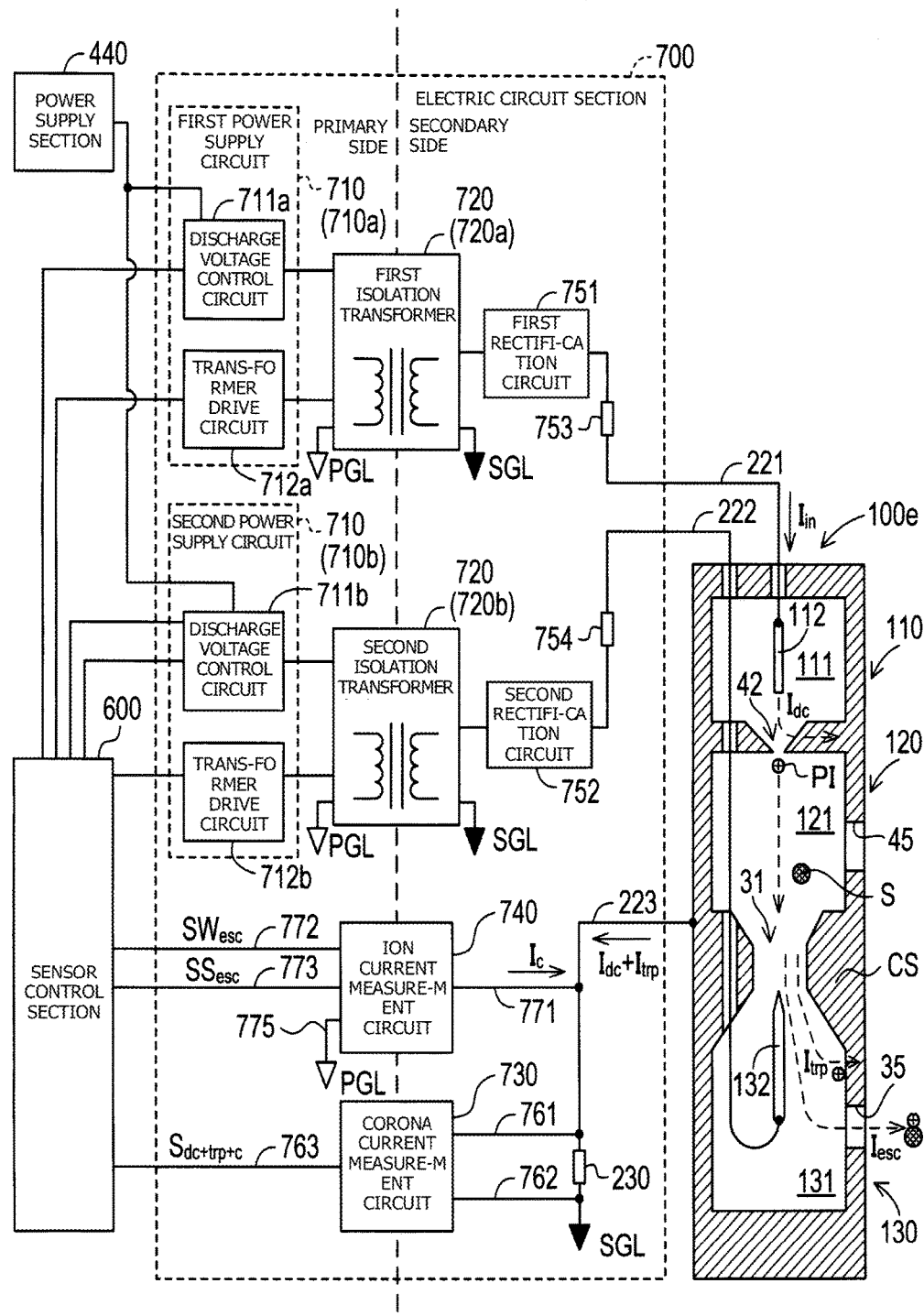
FIG. 3 is an explanatory view exemplifying a general configuration of an electric circuit section.

FIG. 3 is an explanatory view exemplifying a general configuration of the electric circuit section 700.

The electric circuit section 700 includes a power supply circuit 710, an isolation transformer 720, a corona current measurement circuit 730, an ion current measurement circuit 740, a first rectification circuit 751, and a second rectification circuit 752.

The power supply circuit 710 includes a first power supply circuit 710a and a second power supply circuit 710b. The isolation transformer 720 includes a first isolation transformer 720a and a second isolation transformer 720b.

The first power supply circuit 710a steps up the voltage of electric power supplied from the power supply section 440, supplies the stepped up voltage to the first isolation transformer 720a, and drives the first isolation transformer 720a. The first power supply circuit 710a includes a first discharge voltage control circuit 711a and a first transformer drive circuit 712a. The first discharge voltage control circuit 711a is configured such that it can arbitrarily change the voltage value of the electric power supplied to the first isolation transformer 720a under the control by the sensor control section 600. In the present embodiment, the sensor control section 600 controls the voltage value of the electric power supplied to the first isolation transformer 720a such that an input current $I_{in}$ supplied to the first electrode 112 of the particulate sensor 100 through the first wiring line 221 becomes equal to a target current $I_{ta}$ (e.g., 5 µA) set in advance. The method of this control will be described later. As a result, the amount of positive ions PI generated by the corona discharge in the ion generation section 110 can be made constant.

The first transformer drive circuit 712a includes a switch which can switch the flow direction of current flowing through the primary coil of the first isolation transformer 720a. The first transformer drive circuit 712a drives the first isolation transformer 720a by the switching operation of the switch. In the present embodiment, the circuit type of the first isolation transformer 720a is a push-pull type. However, the circuit type of the first isolation transformer 720a is not limited thereto and may be, for example, a half-bridge type or a full-bridge type.

The first isolation transformer 720a performs voltage conversion for the electric power supplied from the first power supply circuit 710a, and supplies the voltage-converted electric power to the first rectification circuit 751 on the secondary side. The first isolation transformer 720a of the present embodiment is configured such that the primary coil and the secondary coil are not in physical contact with each other but are magnetically coupled with each other. A circuit on the primary side of the first isolation transformer 720a includes the sensor control section 600 and the power supply section 440 as well as the first power supply circuit 710a. A circuit on the secondary side of the first isolation transformer 720a includes the particulate sensor 100 and the first rectification circuit 751.

The second power supply circuit 710b steps up the voltage of electric power supplied from the power supply section 440, supplies the stepped up voltage to the second isolation transformer 720b, and drives the second isolation transformer 720b. The second power supply circuit 710b includes a second discharge voltage control circuit 711b and a second transformer drive circuit 712b. The second discharge voltage control circuit 711b is configured such that it can arbitrarily change the voltage value of the electric power supplied to the second isolation transformer 720b under the control by the sensor control section 600. In the present embodiment, the sensor control section 600 controls the voltage value of the electric power supplied to the second isolation transformer 720b such that the voltage supplied to the second electrode 132 of the particulate sensor 100 through the second wiring line 222 becomes equal to a target voltage (e.g., 100 V) set in advance.

The second transformer drive circuit 712b includes a switch which can switch the flow direction of current flowing through the primary coil of the second isolation transformer 720b. The second transformer drive circuit 712b drives the second isolation transformer 720b by the switching operation of the switch. In the present embodiment, the circuit type of the second isolation transformer 720b is a push-pull type. However, the circuit type of the second isolation transformer 720b is not limited thereto and may be, for example, a half-bridge type or a full-bridge type.

The second isolation transformer 720b performs voltage conversion for the electric power supplied from the second power supply circuit 710b, and supplies the voltage-converted electric power to the second rectification circuit 752 on the secondary side. The second isolation transformer 720b of the present embodiment is configured such that the primary coil and the secondary coil are not in physical contact with each other but are magnetically coupled with each other. A circuit on the primary side of the second isolation transformer 720b includes the sensor control section 600 and the power supply section 440 as well as the second power supply circuit 710b. A circuit on the secondary side of the second isolation transformer 720b includes the particulate sensor 100 and the second rectification circuit 752.

The corona current measurement circuit 730 and the ion current measurement circuit 740 are circuits provided between the circuit on the primary side of the isolation transformer 720 (the first isolation transformer 720a and the second isolation transformer 720b) and the circuit on the secondary side of the isolation transformer 720 (the first isolation transformer 720a and the second isolation transformer 720b), and are electrically connected to the primary-side and secondary-side circuits, respectively. As will be described later, the corona current measurement circuit 730 is configured such that a circuit portion electrically connected to the circuit on the primary side of the isolation transformer 720 (the first isolation transformer 720a and the second isolation transformer 720b) is physically insulated from a circuit portion electrically connected to the circuit on the secondary side of the isolation transformer 720 (the first isolation transformer 720a and the second isolation transformer 720b). Here, a ground (ground wiring) which has the reference potential of the primary-side circuit is also referred to as a "primary-side ground PGL," and a ground which has the reference potential of the secondary-side circuit is also referred to as a "secondary-side ground SGL."

Ends of the primary coils of the isolation transformer 720 (the first isolation transformer 720a and the second isolation transformer 720b) are connected to the primary-side ground PGL, and ends of the secondary coils thereof are connected to the secondary-side ground SGL. One end of the signal line 223 is connected to the casing CS, and the other end of the signal line 223 is connected to the secondary-side ground SGL.

The first rectification circuit 751 is connected to the first electrode 112 through a short protection resistor 753, and supplies the converted electric power to the first electrode 112 through the first wiring line 221. Namely, the voltage supplied from the first rectification circuit 751 becomes mostly a discharge voltage at the first electrode 112, and the current supplied from the first rectification circuit 751 becomes an input current $I_{in}$ input to the first electrode 112. The second rectification circuit 752 is connected to the second electrode 132 through a short protection resistor 754, and applies the converted voltage to the second electrode 132 through the second wiring line 222.

The ion current measurement circuit 740 detects the current value of a current ($I_{esc}$) corresponding to the positive ions PI having flowed out without being trapped by the ion trapping section 130 and supplies to the secondary-side circuit a current (compensation current $I_c$) corresponding to the positive ions PI having flowed out. The ion current measurement circuit 740 is connected to the signal line 223 on the secondary side (specifically, a portion of the signal line 223 located between the casing CS and the shunt resistor 230) through a wiring line 771, and is connected to the sensor control section 600 on the primary side through wiring lines 772 and 773. Also, the ion current measurement circuit 740 is connected to the primary-side ground PGL through the wiring line 775. Through the wiring line 772, the ion current measurement circuit 740 outputs to the sensor control section 600 a signal $SW_{esc}$ showing a current value corresponding to the amount of positive ions PI having flowed out without being trapped by the ion trapping section 130. The ion current measurement circuit 740 also outputs a signal $SS_{esc}$ to the sensor control section 600 through the wiring line 773, the signal $SS_{esc}$ being obtained by amplifying the signal $SW_{esc}$ and serving as a high sensitivity signal.

The corona current measurement circuit 730 is connected to the signal line 223 through wiring lines 761 and 762, and is connected to the sensor control section 600 through a wiring line 763. The wiring lines 761 and 762 are connected to the signal line 223 such that the shunt resistor 230 provided in the signal line 223 is located between the wiring lines 761 and 762. The corona current measurement circuit 730 outputs to the sensor control section 600 a signal $S_{dc+trp+c}$ representing the current value of a secondary-side current ($I_{dc}+I_{trp}+I_c$) flowing from the casing CS toward the secondary-side ground SGL through the signal line 223. Here, a "signal representing the current value" is not limited to a signal which directly represents the current value, and may be a signal which indirectly represents the current value. For example, the "signal representing the current value" may be a signal on the basis of which the current value can be specified by applying a computation expression or a map to information obtained from the signal. Notably, since the compensation current $I_c$ supplied (supplemented) from the ion current measurement circuit 740 corresponds to the current corresponding to the positive ions PI having flowed out of the casing CS, the current value of the secondary-side current which includes the compensation current $I_c$ and which flows from the casing CS to the secondary-side ground SGL; i.e., the current value of the secondary-side current ($I_{dc}+I_{trp}+I_c$) flowing through the shunt resistor 230, becomes equal to the current value of the input current $I_{in}$.

Using the signal $S_{dc+trp+c}$ input from the corona current measurement circuit 730, the sensor control section 600 controls the first discharge voltage control circuit 711a such that the current value of the input current $I_{in}$ becomes equal to the target current $I_{ta}$. Namely, the corona current measurement circuit 730 and the sensor control section 600 constitute a constant current circuit for maintaining the current value of the corona current (=the input current $I_{in}$) at a constant level. Since the current value of the corona current correlates with the amount of positive ions PI generated at the ion generation section 110, the amount of positive ions PI generated at the ion generation section 110 is maintained constant by this constant current circuit.

There will be described a method by which the ion current measurement circuit 740 detects the current value of the current corresponding to the positive ions PI having flowed out without being trapped by the ion trapping section 130.

Here, the current supplied from the first wiring line 221 to the first electrode 112 is referred to as "input current $I_{in}$"; the current flowing from the first electrode 112 to the casing CS through the partition wall 42 due to corona discharge is referred to as "discharge current $I_{dc}$"; the current corresponding to the charge of the positive ions PI which are some of the positive ions PI generated due to corona discharge, are used for electrification of the soot S, and leak to the outside of the casing CS will be referred to as "signal current $I_{esc}$"; and the current corresponding to the charge of the positive ions PI trapped by the casing CS is referred to as "trapped current $I_{trp}$." These four currents satisfy the relation of expression (1) shown in the following [F1].

[F1]

$$I_{in}=I_{dc}+I_{trp}+I_{esc} \quad (1)$$

Here, the signal current $I_{esc}$ is a signal which is output from the ion current measurement circuit 740 and which represents a current value corresponding to the current (the compensation current $I_c$) corresponding to the positive ions PI having flowed out. Therefore, by detecting this compensation current $I_c$, the ion current measurement circuit 740 can detect the current value of the current ($I_{esc}$) corresponding to the positive ions PI having flowed out without being trapped by the ion trapping section 130. Notably, the compensation current $I_e$ is also a signal representing the difference between the primary-side ground PGL and the secondary-side ground SGL.

[1-4. Ion Current Measurement Circuit]

Figure 4:
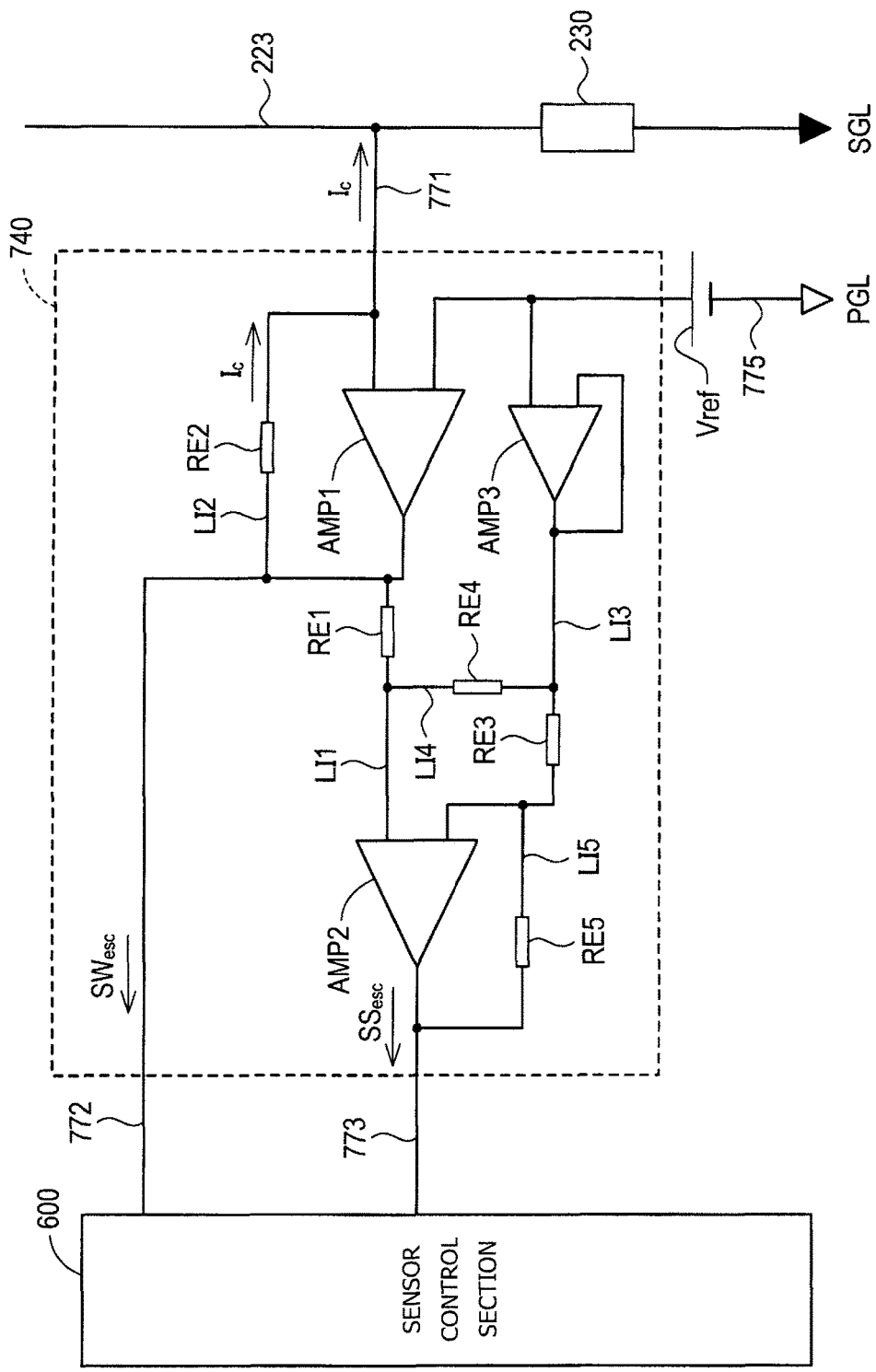
FIG. 4 is an explanatory view exemplifying a general configuration of an ion current measurement circuit.

FIG. 4 is an explanatory view exemplifying a general configuration of the ion current measurement circuit 740.

The ion current measurement circuit 740 includes a first operational amplifier AMP1, a second operational amplifier AMP2, a third operational amplifier AMP3, and resistors RE1 to RE5 having known resistances.

One input terminal of the first operational amplifier AMP1 is connected to the secondary-side ground SGL through the wiring line 771 and the signal line 223 (including the shunt resistor 230), and the other input terminal of the first operational amplifier AMP1 is connected to the primary-side ground PGL through the wiring line 775. The output terminal of the first operational amplifier AMP1 is connected to the sensor control section 600 through the wiring line 772. Notably, a power source Vref for providing a constant reference voltage (for example, 0.5 V) in relation to the primary-side ground PGL is connected to the other input terminal of the first operational amplifier AMP1. By inputting the reference voltage to the first operational amplifier AMP1, it is possible to cause the potential difference between the two input terminals of the first operational amplifier AMP1 to approach a potential difference range within which an error (error due to bias current, offset voltage, etc.) is hardly produced. Also, the output terminal of the first operational amplifier AMP1 is connected to one input terminal of the second operational amplifier AMP2 through a portion of the wiring line 772 and a wiring line LI1, and is connect to the wiring line 771 through a portion of the wiring line 772 and a wiring line LI2. The resistor RE1 is provided in the wiring line LI1, and the resistor RE2 is provided in the wiring line LI2.

One input terminal of the second operational amplifier AMP2 is connected to the first operational amplifier AMP1 through a portion of the wiring line LI1 and the wiring line 772, and the other input terminal of the second operational amplifier AMP2 is connected to the primary-side ground PGL through a wiring line LI3 and the wiring line 775. The resistor RE3 and the third operational amplifier AMP3 are provided in the wiring line LI3. A wiring line LI4 is connected to a node between the resistor RE3 and the third operational amplifier AMP3. The wiring line LI3 is connected to the wiring line LI1 through the wiring line LI4 in which the resistor RE4 is provided. The third operational amplifier AMP3 is configured to function as a voltage follower which suppresses voltage change due to current change on the output side. The output terminal of the second operational amplifier AMP2 is connected to the sensor control section 600 through the wiring line 773, and is connected to the wiring line LI3 through the wiring line 773 and a wiring line LI5. The resistor RE5 is provided in the wiring line LI5.

When a difference is produced between the reference potential of the secondary-side ground SGL and the reference potential of the primary-side ground PGL as a result of generation of the signal current $I_{esc}$, the first operational amplifier AMP1 outputs a voltage corresponding to this difference. Since the voltage output from the first operational amplifier AMP1 correlates with the current value of the signal current $I_{esc}$, this voltage value is output to the sensor control section 600 through the wiring line 772 as a signal $SW_{esc}$ representing the current value of the signal current $I_{esc}$.

Also, the voltage output from the first operational amplifier AMP1 produces the compensation current $I_c$, which is supplied from the wiring line LI2 to the wiring line 771 through the resistor RE2. As described above, the current value of the compensation current $I_c$ is equal to the current value of the signal current $I_{esc}$. Therefore, as a result of supply of the compensation current $I_c$ to the wiring line 771 which constitutes the secondary-side circuit, the difference between the reference potential of the secondary-side ground SGL and the reference potential of the primary-side ground PGL is compensated.

The second operational amplifier AMP2 amplifies the signal $SW_{esc}$ input from the first operational amplifier AMP1, and outputs to the sensor control section 600 the signal $SS_{esc}$ obtained as a result of the amplification. Since the second operational amplifier AMP2 is configured to function as a differential amplification circuit, the second operational amplifier AMP2 outputs a voltage corresponding to the difference between the voltage input to one input terminal as the signal $SW_{esc}$ and the reference potential of the primary-side ground PGL input to the other input terminal. Namely, the second operational amplifier AMP2 outputs a voltage to the sensor control section 600 as the signal $SS_{esc}$, the voltage being obtained by amplifying the voltage of the input signal $SW_{esc}$ at a predetermined amplification factor (e.g., $10^3$ times).

The sensor control section 600 detects the amount of soot S contained in the exhaust gas through use of the signal $SW_{esc}$ (low sensitivity signal) and the signal $SS_{esc}$ (high sensitivity signal) input from the ion current measurement circuit 740. No particular limitation is imposed on the method of detecting the amount of soot S contained in the exhaust gas by using these signals representing the current value of the signal current $I_{esc}$. For example, in the case where the sensor control section 600 stores a map or a relational expression showing the relation between the voltage value of the signal and the amount of soot S contained in the exhaust gas, the sensor control section 600 can calculate the amount of soot S contained in the exhaust gas by using the map or the relational expression.

The sensor control section 600 of the present embodiment obtains each of the voltage values, which are analog signals input thereto as the signals $SS_{esc}$ and $SW_{esc}$, as a digital value of a predetermined resolution (for example, 8 bits). Also, the sensor control section 600 is configured such that the size of the voltage readable range (the range of the full scale) becomes the same for the signals $SS_{esc}$ and $SW_{esc}$ input thereto.

The signal $SS_{esc}$ (high sensitivity signal) has a higher sensitivity (resolution) for the current value of the signal current $I_{esc}$ as compared with the signal $SW_{esc}$ (low sensitivity signal). For example, whereas a voltage level of the signal $SW_{esc}$ of 1 V corresponds to a magnitude of the signal current $I_{esc}$ of 1 nA, a voltage level of the signal $SS_{esc}$ of 1 V corresponds to a magnitude of the signal current $I_{esc}$ of 1 pA. Meanwhile, the sensor control section 600 has the same voltage resolution (the minimum recognizable potential difference) (for example, 0.02 V) for both the signals $SS_{esc}$ and $SW_{esc}$. Accordingly, the current value of the signal current $I_{esc}$ corresponding to the voltage resolution of the sensor control section 600 is small for the case of the signal $SS_{esc}$ (e.g., 0.02 pA) and is large for the case of the signal $SW_{esc}$ (e.g., 0.02 nA). In other words, the sensor control section 600 can detect a smaller change in the signal current $I_{esc}$ from signal $SS_{esc}$, as compared with the signal $SW_{esc}$.

Therefore, the amount of soot S contained in the exhaust gas obtained from the signal $SS_{esc}$ is smaller in the minimum recognizable unit and is higher in accuracy than the amount of soot S contained in the exhaust gas obtained from the signal $SW_{esc}$. Meanwhile, the readable voltage range (e.g., 0 to 5 V) of the sensor control section 600 is set to cover the entire voltage range of the signal $SW_{esc}$. Therefore, a range in which the amount of soot S contained in the exhaust gas can be measured through use of the signal $SW_{esc}$ is wider than a range in which the amount of soot S contained in the exhaust gas can be measured through use of the signal $SS_{esc}$. If the amount of soot S contained in the exhaust gas falls within a range corresponding to the entire voltage range of the signal $SW_{esc}$, the amount of soot S can be measured within the entire range.

As can be understood from the above, when the voltage value of the signal $SS_{esc}$ falls within the readable voltage range, the sensor control section 600 can accurately measure the amount of soot S contained in the exhaust gas through use of the signal $SS_{esc}$, and when the voltage value of the signal $SS_{esc}$ falls outside the readable voltage range, the sensor control section 600 can measure the amount of soot S contained in the exhaust gas through use of the signal $SW_{esc}$ which allows measurement within a wider range.

[1-5. Corona Current Measurement Circuit]

Figure 5:
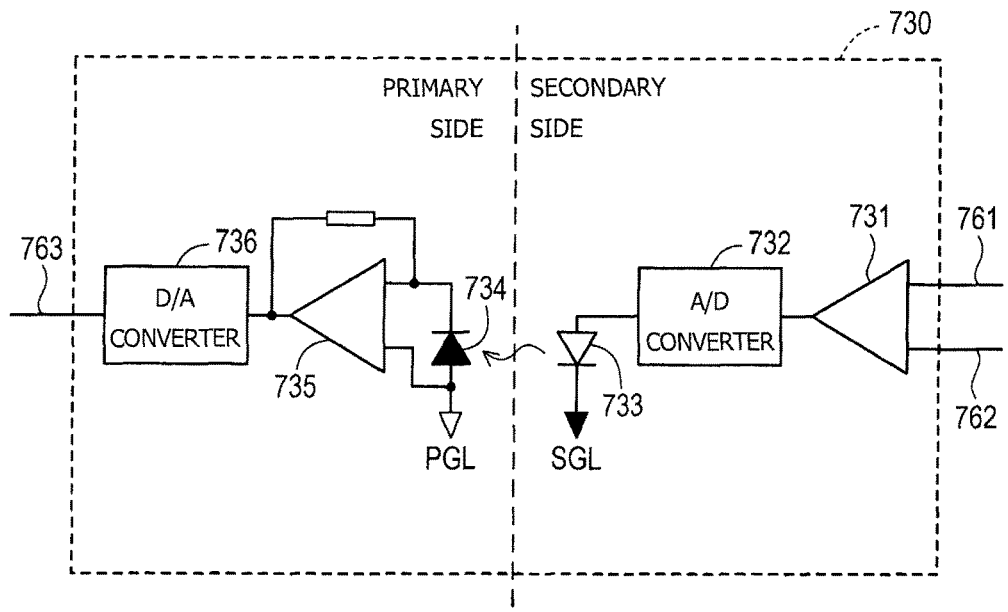
FIG. 5 is an explanatory view exemplifying a general configuration of a corona current measurement circuit.

FIG. 5 is an explanatory view exemplifying a general configuration of the corona current measurement circuit 730.

The corona current measurement circuit 730 is configured as a so-called optical-coupling-type isolation amplifier whose input and output sides are isolated from each other. The input side of the corona current measurement circuit 730 belongs to the secondary side of the electric circuit section 700 (FIG. 3), and the output side of the corona current measurement circuit 730 belongs to the primary side of the electric circuit section 700. The corona current measurement circuit 730 includes a secondary-side operational amplifier 731, an A/D converter 732, a light emitting section 733, a light receiving section 734, a primary-side operational amplifier 735, and a D/A converter 736.

The two input terminals of the secondary-side operational amplifier 731 are connected to the wiring line 761 and the wiring line 762, respectively, and the output terminal thereof is connected to the A/D converter 732. The secondary-side operational amplifier 731 amplifies the potential difference between the wiring line 761 and the wiring line 762 and outputs the amplified potential difference to the A/D converter 732. The potential difference between the wiring line 761 and the wiring line 762 is the potential difference between the opposite ends of the shunt resistor 230 (FIG. 3) whose resistance is known, and correlates with the current value of the current flowing through the signal line 223 (FIG. 3) (the secondary-side current ($I_{dc}+I_{trp}+I_c$)). Namely, the secondary-side operational amplifier 731 amplifies an analogue voltage signal representing the current value of the current flowing through the signal line 223 (FIG. 3) and outputs the amplified analogue voltage signal to the A/D converter 732.

The A/D converter 732, which is connected to the secondary-side operational amplifier 731 and the light emitting section 733, converts the analog signal output from the secondary-side operational amplifier 731 to a digital signal and outputs the digital signal to the light emitting section 733.

The light emitting section 733 includes an LED and is connected to the A/D converter 732 and the secondary-side ground SGL. The light emitting section 733 converts the digital voltage signal output from the A/D converter 732 to an optical signal.

The light receiving section 734 includes a photodiode and is connected to the primary-side operational amplifier 735 and the primary-side ground PGL. The light receiving section 734 converts the optical signal output from the light emitting section 733 to a current signal and outputs the current signal to the primary-side operational amplifier 735. In this manner, the light emitting section 733 and the light receiving section 734 are electrically and physically isolated from each other, and signals are transmitted between the light emitting section 733 and the light receiving section 734 through the mediation of light.

The primary-side operational amplifier 735 is connected to the light receiving section 734 and the D/A converter 736, and includes a current-voltage-conversion circuit. The primary-side operational amplifier 735 convers the current signal output from the light receiving section 734 to a voltage signal and outputs the voltage signal to the D/A converter 736. The D/A converter 736, which is connected to the primary-side operational amplifier 735 and the wiring line 763, converts the digital signal output from the primary-side operational amplifier 735 to an analog signal and outputs the analog signal to the sensor control section 600 (FIG. 3) through the wiring line 763. Since the corona current measurement circuit 730 has the above-described configuration, the corona current measurement circuit 730 can output to the primary-side sensor control section 600 the signal input from the secondary-side signal line 223, while maintaining the isolation between the primary side and the secondary side.

[1-6. Processes Executed by Sensor Control Section]

The sensor control section 600 includes a microcomputer and executes various types of processes.

As one of the various types of processes, the sensor control section 600 executes a particulate measurement process for computing the amount of soot S by using the signals $SS_{esc}$ and $SW_{esc}$ from the ion current measurement circuit 740. Notably, the particulate measurement process includes a step of correcting, through use of correction information B, the ion current A measured on the basis of the signals from the ion current measurement circuit 740.

Figure 6:
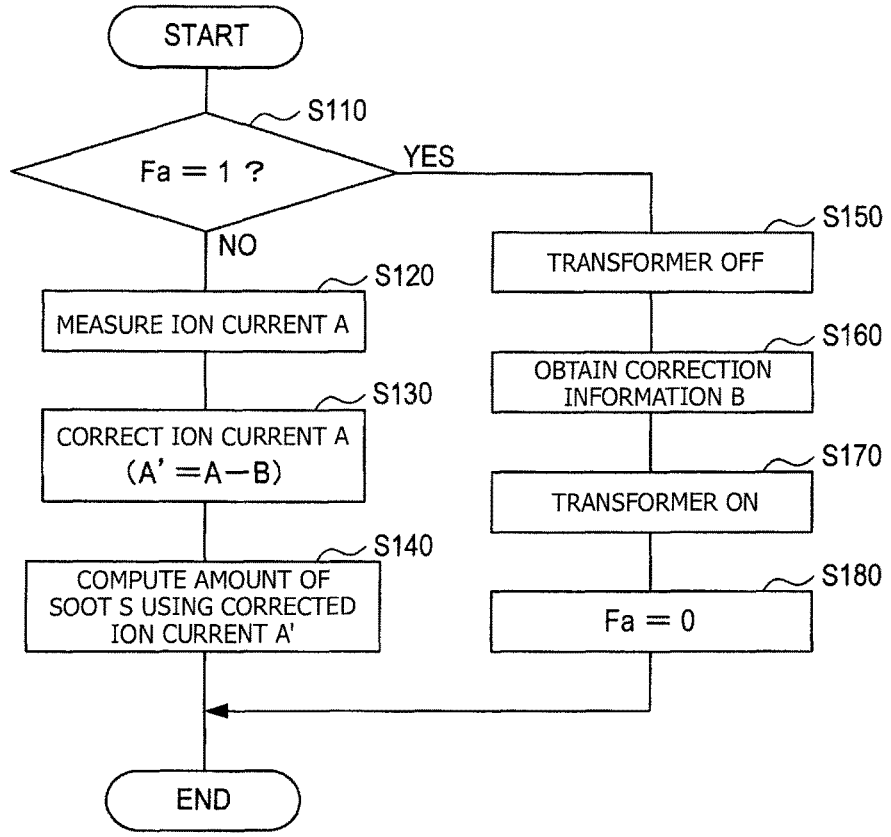
FIG. 6 is a flowchart representing the details of a particulate measurement process.

Here, the details of the particulate measurement process will be described. FIG. 6 is a flowchart representing the details of the particulate measurement process. When the sensor control section 600 is started, the particulate measurement process is repeatedly executed at predetermined intervals (for example, intervals of 100 msec).

In the particulate measurement process, in S110 (S stands for step), the sensor control section 600 first determines whether or not a correction information obtainment flag Fa is in a set state (Fa=1). In the case where the sensor control section 600 makes an affirmative determination, it proceeds to S150. In the case where the sensor control section 600 makes a negative determination, it proceeds to S120.

Notably, the correction information obtainment flag Fa is an internal flag which represents whether or not the present point in time is a timing for obtaining a piece of correction information for correcting the ion current. The correction information obtainment flag Fa is set to the set state (Fa=1) when the sensor control section 600 determines that the correction information obtainment timing has come in an obtainment timing determination process.

Figure 7:
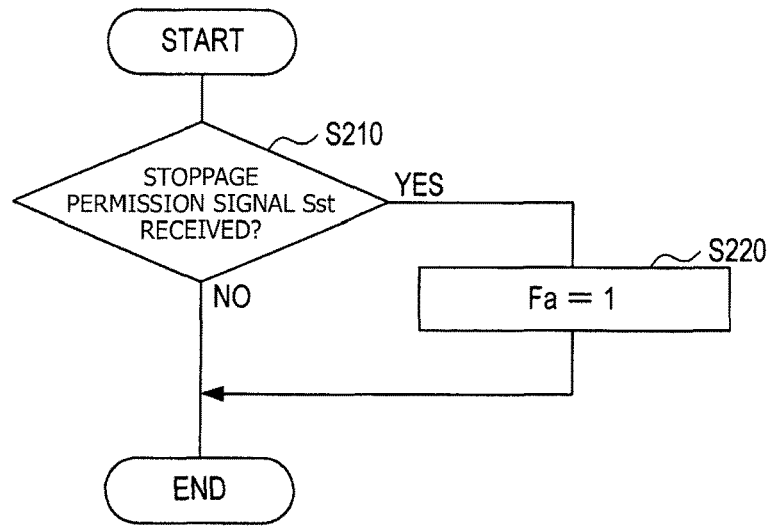
FIG. 7 is a flowchart representing the details of an obtainment timing determination process.

Here, the details of the obtainment timing determination process will be described. FIG. 7 is a flowchart representing the details of the obtainment timing determination process. When the sensor control section 600 is started, the obtainment timing determination process is repeatedly executed at predetermined intervals (for example, intervals of 100 msec).

In the obtainment timing determination process, in S210 (S stands for step), the sensor control section 600 first determines whether or not it has received a stoppage permission signal Sst from the vehicle control section 420. In the case where the sensor control section 600 makes an affirmative determination, it proceeds to S220. In the case where the sensor control section 600 makes a negative determination, it ends the present process.

Notably, the vehicle control section 420 sends the stoppage permission signal Sst to the sensor control section 600 when the operation state of the internal combustion engine 400 is an operation state in which soot is hardly generated in exhaust gas.

In the case where the sensor control section 600 proceeds to S220 as a result of the affirmative determination in S210, in S220, the sensor control section 600 sets the correction information obtainment flag Fa to the set state (Fa=1).

In the case where a negative determination is made in S210 or the process of S220 ends, the obtainment timing determination process ends. Such an obtainment timing determination process is repeatedly executed at predetermined intervals.

The description of the particulate measurement process will be resumed. In the case where the sensor control section 600 proceeds to S120 as a result of the negative determination in S110, in S120, the sensor control section 600 measures the ion current A corresponding to the signal current $I_{esc}$ by using the low sensitivity signal $SW_{esc}$ and the high sensitivity signal $SS_{esc}$ input from the ion current measurement circuit 740.

In the next S130, the sensor control section 600 computes a corrected ion current A' by correcting the ion current A obtained in S120 by using the correction information B. Notably, the correction information B is stored in the storage section (RAM or the like) of the sensor control section 600. The sensor control section 600 reads out the correction information B from the storage section in S130 and uses it for computation of the corrected ion current A'. Notably, in the case where the correction information B has not yet been obtained in S160 to be described later, the sensor control section 600 performs the correction by using a default value (for example, B=500 [pA]) as the correction information B.

In the next S140, the sensor control section 600 computes the amount of soot S contained in the exhaust gas by using the corrected ion current A'.

Notably, for example, a map showing the relation between the corrected ion current A' and the amount of soot S contained in the exhaust gas, a relational expression expressing the relation between the corrected ion current A' and the amount of soot S contained in the exhaust gas, or the like is stored in the storage section (RAM or the like) of the sensor control section 600. In S140, the control section 600 can compute the amount of soot S contained in the exhaust gas by using the map, the relational expression, or the like stored in the storage section.

The sensor control section 600 outputs to the vehicle control section 420 a piece of information regarding the amount of soot S (the amount of particulates) obtained as a result of the computation.

In the case where the sensor control section 600 proceeds to S150 as a result of the affirmative determination in S110, in S150, the sensor control section 600 sets the isolation transformer 720 (the first isolation transformer 720*a* and the second isolation transformer 720*b*) to an OFF state to thereby stop the voltage conversion by the first isolation transformer 720*a* and the second isolation transformer 720*b*.

As a result of this operation, the generation of the positive ions PI in the ion generation section 110 is stopped, and the application of voltage to the second electrode 132 is stopped. Under such conditions, electrification of the soot S (particulates) by the positive ions PI is not performed in the electrification chamber 121 (namely, no electrified particulate is produced). Therefore, the signal current $I_{esc}$ does not change.

In the next S160, the sensor control section 600 computes a current value corresponding to the signal current $I_{esc}$ by using the low sensitivity signal $SW_{esc}$ and the high sensitivity signal $SS_{esc}$ input from the ion current measurement circuit 740, and obtains the result of the computation as correction information B. Also, in S160, the sensor control section 600 performs a process of storing the obtained correction information B in the storage section (RAM or the like) of the sensor control section 600.

In the next S170, the sensor control section 600 sets the isolation transformer 720 (the first isolation transformer 720*a* and the second isolation transformer 720*b*) to an ON state, to thereby resume the voltage conversion by the first isolation transformer 720*a* and the second isolation transformer 720*b*.

As a result, the generation of the positive ions PI in the ion generation section 110 is resumed, and the application of voltage to the second electrode 132 is resumed. Thus, the signal current $I_{esc}$ which changes in accordance with the ions used for the electrification of soot S (in other words, the signal current $I_{esc}$ changing in accordance with the amount of electrified particulates) is generated.

In the next S180, the sensor control section 600 sets the correction information obtainment flag Fa to a reset state (Fa=0).

When the process of S140 or S180 ends, the particulate measurement process ends. Such a particulate measurement process is repeatedly executed at predetermined intervals.

As described above, through execution of the particulate measurement process and the obtainment timing determination process, the sensor control section 600 can obtain the correction information B at the timing of reception of the stoppage permission signal Sst from the vehicle control section 420, and obtain the corrected ion current A' by correcting the ion current A by using the correction information B.

[1-7. Effects]

As described above, the particulate measurement system 10 of the present embodiment is configured such that the particulate measurement process is executed by the sensor control section 600.

The particulate measurement process includes the step (S150) of stopping the voltage conversion by the first isolation transformer 720*a* and the second isolation transformer 720*b*, the step (S160) of obtaining the correction information B, and the step (S130) of correcting the ion current A by using the correction information B.

In the case where the voltage conversion by the first isolation transformer 720*a* and the second isolation transformer 720*b* is stopped as a result of the execution of S150, the generation of the positive ions PI in the ion generation section 110 is stopped, and the application of voltage to the second electrode 132 is stopped.

However, when an improper current flows through particulates or the like (soot or the like) having adhered to the particulate sensor 100, that improper current is detected as a signal current. Therefore, the low sensitivity signal $SW_{esc}$ and the high sensitivity signal $SS_{esc}$ input from the ion current measurement circuit 740 when the voltage conversion by the first isolation transformer 720*a* and the second isolation transformer 720*b* is stopped change in accordance with the improper current. Accordingly, the correction information B obtained in S160 reflects the improper current.

Because of this, it is possible to measure the amount of soot S (the amount of particulates), while suppressing the influence of the improper current, by correcting the ion current A (the signal current $I_{esc}$) detected in S120 through use of the correction information B and computing the amount of soot S through use of the corrected ion current A' (S140).

Therefore, since the particulate measurement system 10 can measure the amount of soot S (the amount of particulates), while suppressing the influence of the improper current, by obtaining the corrected ion current A' by correcting the ion current A through use of the correction information B, the particulate measurement system 10 can suppress a decrease in the accuracy of measurement of the amount of soot S due to improper current.

Next, the particulate measurement system 10 is configured such that the obtainment timing determination process and the particulate measurement process are executed by the sensor control section 600. In the obtainment timing determination process, when the stoppage permission signal Sst is received from the vehicle control section 420, the correction information obtainment flag Fa is set to the set state (Fa=1). In the particulate measurement process, when the correction information obtainment flag Fa is set to the set state, the isolation transformer 720 (the first isolation transformer 720a and the second isolation transformer 720b) is set to the OFF state (S150), and the result of computation of the current value corresponding to the signal current $I_{esc}$ is obtained as the correction information B.

Namely, the particulate measurement system 10 is configured such that, when the sensor control section 600 which executes the obtainment timing determination process and the particulate measurement process receives the stoppage permission signal Sst from the vehicle control section 420, the isolation transformer 720 is set to the OFF state so as to stop the voltage conversion by the isolation transformer 720.

Notably, the vehicle control section 420, which controls the state of combustion in the internal combustion engine 400, the amount of fuel supplied to the engine, etc., can determine whether or not the operation state of the internal combustion engine is an operation state in which exhaust gas contains no soot S (or an operation state in which the amount of soot S is small). When the exhaust gas contains no soot S (or when the amount of soot S is small), the vehicle control section 420 sends the stoppage permission signal Sst to the sensor control section 600. In this manner, the vehicle control section 420 informs the sensor control section 600 of the time of permission of the stoppage of the voltage conversion by the isolation transformer 720.

Therefore, the sensor control section 600 can determine whether or not the present point in time is the time at which exhaust gas contains no soot S (the time at which the amount of soot S is small) by receiving the stoppage permission signal Sst from the vehicle control section 420. As a result, the sensor control section 600 can obtain the correction information B while avoiding times at which soot S is likely to be generated (in other words, timings at which the necessity of measuring the amount of soot S is high).

Accordingly, since the particulate measurement system 10 can avoid an increase in the time over which the measurement of soot S is stopped in a period during which the necessity of measuring the amount of soot S is high, the particulate measurement system 10 can suppress a decrease in the accuracy of measurement of soot S.

[1-8. Correspondence of Wording]

Here, the correspondence of wording will be described.

The particulate measurement system 10 corresponds to an example of the particulate measurement system; the particulate sensor 100 corresponds to an example of the particulate sensor; the sensor drive section 300 corresponds to an example of the sensor drive section; the ion generation section 110 corresponds to an example of the ion generation section; the electrification chamber 121 corresponds to an example of the electrification chamber, and the ion trapping section 130 corresponds to an example of the trapping section.

The first isolation transformer 720a corresponds to an example of the isolation transformer for corona discharge; the sensor control section 600 and the corona current measurement circuit 730 correspond to an example of the corona discharge control section.

The sensor control section 600 executing S120 and the ion current measurement circuit 740 correspond to an example of the particulate computation section; the sensor control section 600 executing S110 and S150 corresponds to an example of the voltage conversion stoppage section; the sensor control section 600 executing S160 corresponds to an example of the correction information obtaining section; and the sensor control section 600 executing S130 corresponds to an example of the correction section.

[2. Second Embodiment]

In the above-described embodiment, the determination process (the determination process (S110) of determining whether to set the isolation transformer to the OFF state or whether to obtain the correction information B) in the particulate measurement process is a determination process which makes a determination on the basis of only the state of the correction information obtainment flag Fa. However, the present invention is not limited to such an embodiment.

An example of the particulate measurement process which employs a different determination method is a second particulate measurement process which includes a determination process which makes a determination on the basis of not only the state of the correction information obtainment flag Fa but also the result of a determination as to whether or not the present time is the time of initial startup of the apparatus.

In view of the above, as a second embodiment, there will be described a particulate measurement system which is similar to the particulate measurement system of the first embodiment but which has a sensor control section which executes a second particulate measurement process instead of the particulate measurement process Notably, since the particulate measurement system of the second embodiment is identical with that of the first embodiment except the point that the particulate measurement process is replaced with the second particulate measurement process, the second particulate measurement process will be mainly described, and description of the common structure is omitted.

Figure 8:
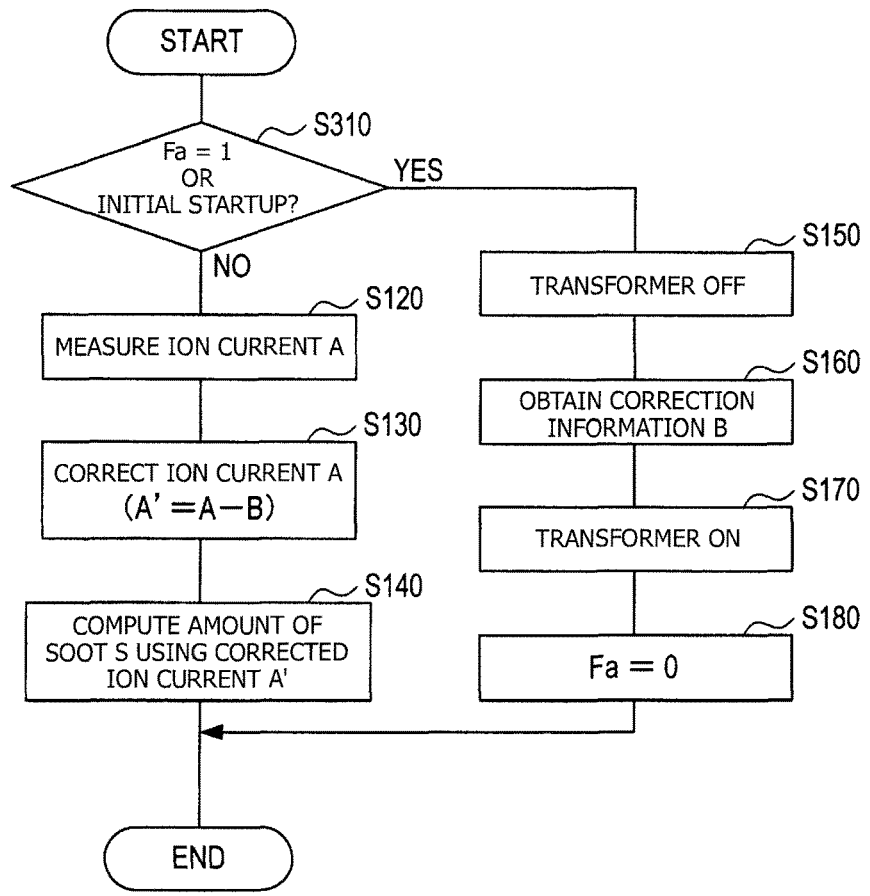
FIG. 8 is a flowchart representing the details of a second particulate measurement process.

Here, the details of the second particulate measurement process will be described. FIG. 8 is a flowchart representing the details of the second particulate measurement process. When the sensor control section 600 is started, like the particulate measurement process of the first embodiment, the second particulate measurement process is repeatedly executed at predetermined intervals (for example, intervals of 100 msec).

In the second particulate measurement process, in S310 (S stands for step), the sensor control section 600 first determines whether or not the correction information obtainment flag Fa is in the set state (Fa=1) and determines whether or not the particulate measurement system (or the sensor control section) is in an initial startup state. In the case where the correction information obtainment flag Fa is in the set state (Fa=1) or the particulate measurement system (or the sensor control section) is in the initial startup state, the sensor control section 600 makes an affirmative determination. In other cases, the sensor control section 600 makes a negative determination. In the case where the sensor control section 600 makes an affirmative determination in S310, it proceeds to S150. In the case where the sensor control section 600 makes a negative determination in S310, it proceeds to S120.

Here, the determination as to whether or not the particulate measurement system (or the sensor control section) is in the initial startup state is made by determining whether or not S310 is executed for the first time after the startup of the particulate measurement system (or the sensor control section). In the case where S310 is executed for the first time, the result of the determination in S310 becomes an affirmative determination.

Since the details of the processes in S120 to S180 subsequent thereto are identical with those in S120 to S180 of the particulate measurement process of the first embodiment, their descriptions are omitted.

In the particulate measurement system having the sensor control section which executes such a second particulate measurement process, after the startup of the particulate measurement system (or the sensor control section), the sensor control section 600 executes the process (S160) of executing the process of obtaining the correction information B, irrespective of the state of the correction information obtainment flag Fa, in the case where S310 of the second particulate measurement process is executed for the first time.

Notably, since the particulate measurement system (the sensor control section) starts as a result of the startup of the internal combustion engine, in S310 of the second particulate measurement process, the sensor control section 600 can determine whether or not the present point in time is immediately after the startup of the internal combustion engine 400.

As a result, the particulate measurement system executing the second particulate measurement process can obtain the correction information B immediately after the startup of itself (in other words, immediately after the startup of the internal combustion engine) without waiting for the stoppage permission signal Sst from the vehicle control section 420. Therefore, even when the particulate measurement system is started after elapse of a long period of time after the previous startup, the particulate measurement system can obtain the correction information B corresponding to the newest state of the particulate sensor immediately after the startup, and can correct the ion current A properly.

Also, since this particulate measurement system obtains the correction information B immediately after the startup and also obtains the correction information B when it receives the stoppage permission signal Sst from the vehicle control section 420, the particulate measurement system can update the correction information B in accordance with a change in the state of the particulate sensor (a change in the improper current).

Accordingly, since this particulate measurement system can obtain the correction information B and can obtain the corrected ion current A' in accordance with the state of the particulate sensor immediately after the startup and a change in the state of the particulate sensor (a change in the improper current) after that, the particulate measurement system can suppress a decrease in the accuracy of measurement of the amount of soot S due to improper current.

[3. Third Embodiment]

In the above-described embodiment, in the obtainment timing determination process, the determination as to whether to set the correction information obtainment flag Fa to the set state (Fa=1) is made by determining whether or not the stoppage permission signal Sst has been received from the vehicle control section 420. However, the present invention is not limited to such an embodiment.

An example of the obtainment timing determination process which employs a different determination method is a second obtainment timing determination process which determines whether to set the correction information obtainment flag Fa to the set state (Fa=1) on the basis of the operation time of the particulate measurement system (the sensor control section).

In view of the above, as a third embodiment, there will be described a particulate measurement system which is similar to the particulate measurement system of the first embodiment but which has a sensor control section which executes a second obtainment timing determination process instead of the obtainment timing determination process.

Notably, since the particulate measurement system of the third embodiment is identical with that of the first embodiment except the point that the obtainment timing determination process is replaced with the second obtainment timing determination process, the second obtainment timing determination process will be mainly described, and description of the common structure is omitted.

Figure 9:
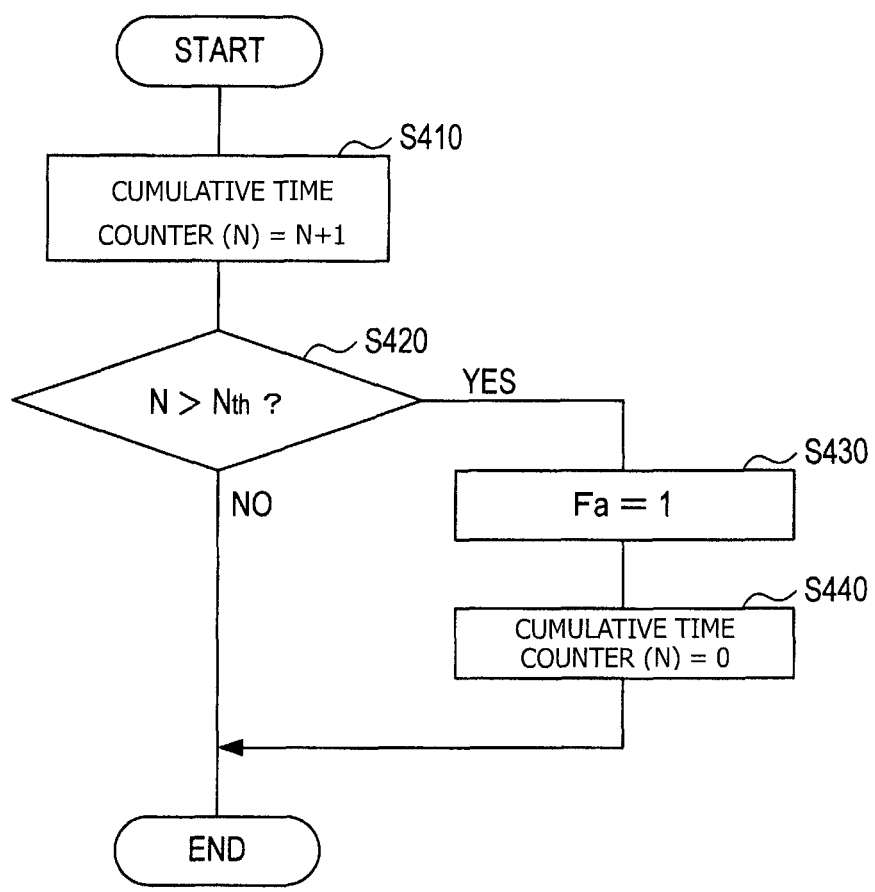
FIG. 9 is a flowchart representing the details of a second obtainment timing determination process.

Here, the details of the second obtainment timing determination process will be described. FIG. 9 is a flowchart representing the details of the second obtainment timing determination process. When the sensor control section 600 is started, like the obtainment timing determination process of the first embodiment, the second obtainment timing determination process is repeatedly executed at predetermined intervals (for example, intervals of 100 msec).

In the second obtainment timing determination process, in S410 (S stands for step), the sensor control section 600 first executes a process of adding 1 to a cumulative time counter N (N=N+1).

Notably, the cumulative time counter N is stored in a nonvolatile storage section of the storage section of the particulate measurement system (sensor control apparatus). The nonvolatile storage section can maintain the stored data even when the system stops. A value is added thereto every time S410 of the second obtainment timing determination process is executed. Therefore, the cumulative time counter N shows a value corresponding to the cumulative operation time of the particulate measurement system (sensor control apparatus) and also shows a value corresponding to the cumulative operation time of the internal combustion engine.

In the next S420, the sensor control section 600 compares the cumulative time counter N and a cumulative determination value Nth set in advance. In the case where the cumulative time counter N is greater than the cumulative determination value Nth, the sensor control section 600 makes an affirmative determination. In the case where the cumulative time counter N is equal to or less than the cumulative determination value Nth, the sensor control section 600 makes a native determination. In the case where the sensor control section 600 makes an affirmative determination in S420, it proceeds to S430. In the case where the sensor control section 600 makes a negative determination in S420, it ends the second obtainment timing determination process.

Notably, "$1\times10^6$" is set to the cumulative determination value Nth of the present embodiment. As a result, every time a stoppage time Tth (=Nth×100 mSec) obtained by multiplying the cumulative determination value Nth by the execution interval (100 mSec) of the second obtainment timing determination process elapses, the sensor control section 600 makes an affirmative determination in S420.

In the case where the sensor control section 600 proceeds to S430 as a result of the affirmative determination in S420, in S430, the sensor control section 600 sets the correction information obtainment flag Fa to the set state (Fa=1).

In the next S440, the sensor control section 600 resets the cumulative time counter N (N=0).

In the case where the sensor control section 600 makes a negative determination in S420 or ends the process of S440, it ends the second obtainment timing determination process. As in the case of the first embodiment, such a second obtainment timing determination process is repeatedly executed at predetermined intervals.

In the particulate measurement system having the sensor control section which executes such a second obtainment timing determination process, when the cumulative operation time T1 (=N×100 mSec) of the internal combustion engine exceeds the stoppage time Tth (affirmative determination in S420), the correction information obtainment flag Fa is set to the set state (S430). As a result, in the particulate measurement process, the process (S150) of stopping the voltage conversion by the isolation transformer 720 and the process (S160) of obtaining the correction information B are executed.

In the case of the particulate sensor 100 attached to the exhaust pipe 402 of the internal combustion engine 400, particulates such as soot contained in exhaust gas may adhere to the particulate sensor 100, and the longer the operation time of the internal combustion engine 400, the greater the possibility of adhesion of the particulates.

Therefore, by stopping the voltage conversion and obtaining the correction information B at the timing at which the cumulative operation time T1 of the internal combustion engine 400 exceeds the stoppage time Tth, it is possible to obtain the correction information B corresponding to the state of adhesion of soot S (particulates) in the particulate sensor 100 and the state of time-course deterioration of the particulate sensor 100. As a result, it is possible to obtain the correction information B corresponding to the state of adhesion of soot S in the particulate sensor 100, and it is possible to properly correct the amount of soot S in accordance with the state of adhesion of soot S in the particulate sensor 100 and the state of time-course deterioration of the particulate sensor 100.

Accordingly, the particulate measurement system of the third embodiment can properly correct the amount of soot S in accordance with the state of adhesion of soot S in the particulate sensor 100 and the state of time-course deterioration of the particulate sensor 100, to thereby suppress a decrease in the accuracy in measuring the soot S.

[4. Other Embodiments]

Embodiments of the present invention has been described; however, the present invention is not limited to the above-described embodiments and can be implemented in various forms without departing from the gist of the invention.

For example, the determination process (the determination process (S110) of determining whether to set the isolation transformer to the OFF state or determining whether to obtain the correction information B) in the particulate measurement process is not limited to the above-described embodiments. An example of a determination process other than those described above is a determination process which performs the determination to obtain the correction information B at predetermined stoppage intervals during a single period of operation of the particulate measurement system (sensor control apparatus).

By stopping the voltage conversion periodically as described above, it is possible to periodically obtain the correction information B and correct the amount of particulates (soot S) on the basis of the correction information B updated at the stoppage intervals. As a result, even in an application in which particulates are measured over a long period, since the correction information is updated at the stoppage intervals, the amount of particulates can be corrected properly irrespective of a change in the state of the particulate sensor (in other words, a change in the state of adhesion of particulates, etc.).

Therefore, according to this particulate measurement system, even when the state of adhesion of particulates, etc. in the particulate sensor changes, the amount of particulates can be corrected properly, whereby a decrease in the particulate measurement accuracy can be suppressed.

Next, in the above-described embodiments, regarding the correction information B, there has been described an embodiment in which the signal current $I_{esc}$ (the ion current A) at the time when the isolation transformer 720 is in the OFF state is obtained as the correction information B. However, the present invention is not limited to such an embodiment. For example, there can be employed an embodiment in which, in place of the signal current $I_{esc}$ (the ion current A), the amount of particulates (the amount of soot S) is obtained as the correction information B, and the amount of particulates (the amount of soot S) is corrected through use of the correction information B.

Specifically, when the voltage conversion by the isolation transformer 720 is stopped, the amount of particulates is computed through use of the signal current $I_{esc}$ (the ion current A), and the amount of particulates is set as the correction information B. When the voltage conversion by the isolation transformer 720 is performed, the amount of particulates is computed through use of the signal current $I_{esc}$ (the ion current A), and the amount of particulates is corrected through use of the correction information B, whereby "the corrected amount of particulates" is obtained.

Also, in the above-described embodiments, the particulate sensor 100 has the second electrode 132. However, the particulate sensor may be configured without use of the second electrode 132. Even when the second electrode 132 is omitted, the amount of particulates can be measured on the basis of the amount of electrified particulates, and the structure of the particulate sensor can be made simpler to a degree corresponding to the omission of the second electrode 132. In such a case, the second power supply circuit 710b, the second isolation transformer 720b, the second rectification circuit 752, the short protection resistor 754, and the second wiring line 222 may be omitted from the electric circuit section 700.

Also, the structure of the particulate sensor which constitutes the particulate measurement system is not limited to the structure in which the ion generation section is disposed in line outside the exhaust gas electrification section. For example, there can be employed a structure in which the ion generation section is disposed inside the exhaust gas electrification section. Further, in the case where the particulate sensor constituting the particulate measurement system is configured such that the ion generation section is disposed inside the exhaust gas electrification section, the air supply section may be omitted from the sensor drive section, and the particulate sensor may have a structure in which the supply of high-pressure air to the electrification chamber by the air supply section is not performed. For example, such a particulate sensor may have a sensor structure disclosed in Japanese Patent Application Laid-Open (kokai) No. 2015-129711 of a patent application filed by the applicant of the present application, and the entirety of the disclosure is incorporated herein by reference. Also, the corona current measurement circuit is not limited to the optical-coupling-type isolation amplifier and may be, for example, a magnetic-coupling-type or capacitive-coupling-type isolation amplifier.

[Description of Symbols]

10 . . . particulate measurement system; 100 . . . particulate sensor; 110 . . . ion generation section; 111 . . . ion generation chamber; 112 . . . first electrode; 120 . . . exhaust gas electrification section; 121 . . . electrification chamber; 130 . . . ion trapping section; 131 . . . trapping chamber; 132 . . . second electrode; 300 . . . sensor drive section;

400 . . . internal combustion engine; 402 . . . exhaust pipe; 420 . . . vehicle control section; 600 . . . sensor control section; 700 . . . electric circuit section; 710 . . . power supply circuit; 710a . . . first power supply circuit; 710b . . . second power supply circuit; 711a . . . first discharge voltage control circuit; 711b . . . second discharge voltage control circuit; 712a . . . first transformer drive circuit; 712b . . . second transformer drive circuit; 720 . . . isolation transformer; 720a . . . first isolation transformer; 720b . . . second isolation transformer; 730 . . . corona current measurement circuit; 740 . . . ion current measurement circuit; CS . . . casing; PGL . . . primary-side ground; PI . . . positive ion; and SGL . . . secondary-side ground.

The invention claimed is:

1. A particulate measurement system for measuring an amount of particulates contained in a target gas, the system comprising:
   a particulate sensor that is configured to detect particulates; and
   a sensor drive section that is configured to drive the particulate sensor, wherein the particulate sensor includes:
      an ion generation section that generates ions by means of corona discharge, an electrification chamber that electrifies at least a portion of the particulates contained in the target gas through use of the ions to thereby produce electrified particulates; and
      a trapping section which traps at least a portion of the ions generated by the ion generation section but not used for electrification of the particulates, the sensor drive section includes:
      an isolation transformer for corona discharge which has a primary coil and a secondary coil and performs voltage conversion of electric power used for the corona discharge, the secondary coil being connected to the ion generation section;
      a particulate computation section which detects a signal current flowing between a primary-side reference potential showing a reference potential of the primary coil of the isolation transformer for corona discharge and a secondary-side reference potential showing a reference potential of the secondary coil of the isolation transformer for corona discharge, the signal current flowing in accordance with the amount of the electrified particulates;
      a corona discharge control section which detects a secondary-side current flowing from the trapping section to the secondary-side reference potential and controls the amount of electric power supplied from the isolation transformer for corona discharge to the ion generation section through use of the secondary-side current such that the amount of ions generated from the ion generation section approaches a predetermined target value;
      a voltage conversion stoppage section which stops the voltage conversion by the isolation transformer for corona discharge;
      a correction information obtaining section which operates, when the voltage conversion is stopped by the voltage conversion stoppage section, so as to obtain correction information based on the amount of the particulates computed by the particulate computation section; and
      a correction section which operates, when the voltage conversion by the isolation transformer for corona discharge is performed, so as to correct, through use of the correction information, the amount of the particulates computed by the particulate computation section,
   the particulate sensor is attached to an exhaust pipe of an internal combustion engine,
   the voltage conversion stoppage section stops the voltage conversion when a cumulative operation time of the internal combustion engine exceeds a predetermined stoppage time, and
   a length of the cumulative operation time is proportional to an amount of adhesion of the particulates to the particulate sensor.

2. The particulate measurement system according to claim 1, wherein the correction information obtaining section obtains the correction information that corresponds to a state of adhesion of particulates to the particulate sensor.

3. The particulate measurement system according to claim 1, wherein the correction information obtaining section obtains the correction information that corresponds to a state of time-course deterioration of the particulate sensor.

4. The particulate measurement system according to claim 1, wherein the correction information obtaining section obtains the correction information that corresponds to a state of time-course deterioration of circuit components of the sensor drive section.

5. The particulate measurement system according to claim 1, wherein the correction information reflects an improper current that flows through particulates having adhered to the particulate sensor.

6. A particulate measurement system for measuring an amount of particulates contained in a target gas, the system comprising:
   a particulate sensor that is configured to detect particulates; and
   a sensor drive section that is configured to drive the particulate sensor, wherein
   the particulate sensor includes:
      an ion generation section that generates ions by means of corona discharge, an electrification chamber that electrifies at least a portion of the particulates contained in the target gas through use of the ions to thereby produce electrified particulates, and
      a trapping section which traps at least a portion of the ions generated by the ion generation section but not used for electrification of the particulates,
   the sensor drive section includes:
      an isolation transformer for corona discharge which has a primary coil and a secondary coil and performs voltage conversion of electric power used for the corona discharge, the secondary coil being connected to the ion generation section,
      a particulate computation section which detects a signal current flowing between a primary-side reference potential showing a reference potential of the primary coil of the isolation transformer for corona discharge and a secondary-side reference potential showing a reference potential of the secondary coil of the isolation transformer for corona discharge, the signal current flowing in accordance with the amount of the electrified particulates,
      a corona discharge control section which detects a secondary-side current flowing from the trapping section to the secondary-side reference potential and controls the amount of electric power supplied from the isolation transformer for corona discharge to the ion generation section through use of the secondary-side current such that the amount of ions generated from the ion generation section approaches a predetermined target value, a voltage conversion stoppage section which stops the voltage conversion by the isolation transformer for corona discharge, a correction information obtaining section which operates, when the voltage conversion is stopped by the voltage conversion stoppage section, so as to obtain correction based on the signal current detected by the particulate computation section or the amount of the particulates computed by the particulate computation section, a correction section which operates, when the voltage conversion by the isolation transformer for corona discharge is performed, so as to correct, through use of the correction information, the signal current detected by the particulate computation section or the amount of the particulates computed by the particulate computation section, the particulate sensor is attached to an exhaust pipe of an internal combustion engine and connected to a vehicle control section, and the voltage conversion stoppage section stops the voltage conversion when receiving a stoppage permission signal from the vehicle control section indicating that no particulate is generated, or particulates are hardly generated in exhaust gas.

* * * * *